US00PP13082P2

(12) United States Plant Patent
Sanders-van Harn

(10) Patent No.: US PP13,082 P2
(45) Date of Patent: Oct. 15, 2002

(54) COTINUS PLANT NAMED 'ANCOT'

(76) Inventor: Adriana Christina Bastiana Sanders-van Harn, Halve Raak 46 2771 AD, Boskoop (NL)

( * ) Notice: Subject to any disclaimer, the term of this patent is extended or adjusted under 35 U.S.C. 154(b) by 0 days.

(21) Appl. No.: 09/728,886

(22) Filed: Dec. 2, 2000

(65) Prior Publication Data

US 2002/0069439 P1 Jun. 6, 2002

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database 2001/04, Aug. 6, 2001, GTI Jouve Retrieval Software, Citation for Cotinus 'Ancot'.*

* cited by examiner

*Primary Examiner*—Bruce R. Campell
*Assistant Examiner*—June Hwu
(74) *Attorney, Agent, or Firm*—Mark P. Bourgeois

(57) ABSTRACT

A new and distinct cultivar of *Cotinus coggygria* named 'Ancot' that is distinguishable from all other varieties of Cotinus, by its spring and summer display of golden yellow leaves suffused with lime-green color. The leaves change color during fall to include amber, burgundy, scarlet and green before the tree becomes deciduous in winter.

3 Drawing Sheets

BOTANICAL CLASSIFICATION

*Cotinus coggygria* cultivar Ancot.

BACKGROUND OF THE INVENTION

The present invention relates to a new and distinct cultivar of *Cotinus coggygria* and referred to hereinafter by the cultivar name 'Ancot'. The new variety was discovered by the inventor in a cultivated area of Boskoop, The Netherlands in 1989. The inventor selected the seedling, which exhibited phenotypic variation, from a seedling batch of *Cotinus coggygria* (not patented) seed.

'Ancot' is distinguished from all other existing *Cotinus coggygria* (not patented) varieties by its golden yellow leaves suffused with lime-green coloring. They remain this color from spring through summer. In fall the leaves turn different colors including amber, burgundy, scarlet and green, before becoming deciduous as winter approaches. Thus far, no flowers have been exhibited by the new Cotinus cultivar 'Ancot'.

The first asexual propagation was done by cuttings in 1990 by the inventor in Boskoop, The Netherlands. Since that time all subsequent generations have been found to be fixed and stable.

SUMMARY OF THE INVENTION

The following characteristics represent the distinguishing traits of the new variety of *Cotinus coggygria* named 'Ancot':

1. The foliage in spring and summer is golden yellow suffused with lime-green coloring.

2. The leaves change to several different colors in fall including the colors amber, scarlet, burgundy and green.

3. No flowering has been observed thus far.

4. 'Ancot' is deciduous in winter.

BRIEF DESCRIPTION OF THE DRAWINGS

The accompanying colored photographs illustrate the overall appearance of the new variety.

Sheet 1 illustrates the entire plant from a front view showing the habit, form, shape and foliage in spring and summer.

Sheet 2 is a close-up view of the foliage exhibited in spring and summer.

Sheet 3 illustrates the changes in leaf color during the fall months. All photographs are taken of plants grown in fifteen-gallon containers that were then transplanted into a garden setting. The prints are made using conventional photographic techniques and although foliage colors in photographs may appear different from actual colors due to light reflectance, they are as accurate as possible by conventional photography.

BOTANICAL DESCRIPTION OF THE PLANT

The following is a detailed botanical description of the new cultivar of Cotinus, named 'Ancot'. Observations, measurements, values, and comparisons were collected in Arroyo Grande, Calif. from a 4 year old plant grown in a fifteen-gallon container and subsequently transplanted in the ground into a garden setting. This particular tree has been observed over a four-year period and has not exhibited flowers thus far. There has also been no flowering observed on the original specimen, by the inventor. The new *Cotinus coggygria* plant has not been observed under all possible environmental conditions. The phenotype may vary with variations in the environment such as temperature and light level, without, however, any variance in genotype. Color references are made to The Royal Horticultural Society Colour Chart except where general terms of ordinary dictionary significance are used. The growing requirements are similar to the species and no growing problems have been observed.

Botanical classification: *Cotinus coggygria* 'Ancot'.
Common name: Smoke bush.
Parentage: A seedling selection of *Cotinus coggygria* (not patented).
Propagation: Tissue culture and cuttings.
Type: Large deciduous shrub or small deciduous tree.
Use: Specimen plant.
Shape: Urn to round.
Growth habit: Bushy and round.
Vigour: Vigorous.
Branching habit: Broad, upright and orthocladus.
Flowering season: Unknown. No flowering has been observed by the inventor to date.
Hardiness: Zone 4 to 8.
Root system: Wide spreading.
Seasonal interest: Spring, summer and fall foliage color.
Special needs: None observed.
Soil types: Rocky nutrient poor, gravelly soils.
Light levels: Prefers full sun. The yellow leaves do not burn in full sun when planted in moisture-retaining soil.
Plant height: 2 meters in height.
Plant width: 1½ meters in width.
Cropping time: 12 weeks for a cutting to develop roots and 1 year to reach one-gallon container from a rooted cutting.
Main trunk size: 4–6 cm in diameter.
Main trunk color: 199A.
Color of lenticels: on trunk: 200A.
Dimensions of lenticels: 7 mm. in width to 8 mm. in length.
Stem:
*Shape.*—Cylindrical.
*Color.*—144 A, B.
*Diameter of secondary stems.*—0.75 cm in diameter.
*Young stem color.*—Exposed side brownish-pink. Ranging from 199A, B, C to D with a tinge of 186A.
*Presence of markings.*—Lenticels.
*Color of lenticels.*—174A with some having pink centers of 186A and B.
*Dimensions of lenticels.*—1 mm. in width by 1 mm. in length.
*Shape of lenticels.*—Lense-shaped to round.
*Internode length.*—1 cm. to 5 cm. between nodes.
*Surface.*—Glabrous and glossy.
*Fragrance.*—Sweet resinous lemon-lime scent when stem is cut.
Foliage:
*Leaf arrangement.*—Most are alternate with younger leaves almost opposite and sinistrorse (spiraling up stem).
*Leaf division.*—Simple.
*Leaf margins.*—Entire, edentate and involute (young leaves are more significantly involute than mature leaves).
*Leaf shape.*—Orbicular and wavy.
*Leaf base.*—Rounded to truncate.
*Leaf tip.*—Obtuse to truncate.
*Upper leaf texture.*—Glabrous.
*Lower leaf texture.*—Glabrous.
*Leaf venation.*—Prominent mid-vein with secondary veins branching off and small dendritic veins near leaf margin.
*Vein surface* (*upper side of leaf*).—Protruding but flattened.
*Vein surface* (*lower leaf surface*).—Protruding.
*Vein color* (*upper*).—11A.
*Vein color* (*lower*).—11B.
*Leaf color upper surface* (*spring and summer*).—143C, 144A, 162A and B with tinges of 167D.
*Leaf color lower surface* (*spring and summer*).—143C, 144A and B, 11A and B, 162A and B with tinges of 167D.
*Leaf color on both surfaces* (*fall*).—Colors include the following range 183A and B, 185A, 180A, 179C, 161A and B, 163C, 60A.
*Leaf length.*—7 cm. in length.
*Leaf width.*—7 cm. in width.
*Attachment.*—Long and petiolate.
*Petiole length.*—5.5 cm. to 6 cm. in length.
*Petiole width.*—2 mm. in width.
*Petiole color.*—144A and B.
*Color of stipules.*—144A and B.
*Dimensions of stipules.*—1 mm. in width by 1 mm. in length.
*Foliar fragrance.*—Slightly sweet resinous lemon-lime scent when bruised.
Leaf bud:
*Leaf bud shape.*—Globose.
*Leaf bud diameter.*—1.5 mm.
*Leaf bud length.*—1.5 mm.
*Leaf bud color.*—144A with tinges of 181A in the middle, tip 200A.
Flower: No flowering has been observed by the inventor to date.

I claim:

1. A new and distinct cultivar of *Cotinus coggygia* plant named 'Ancot' as described and illustrated.

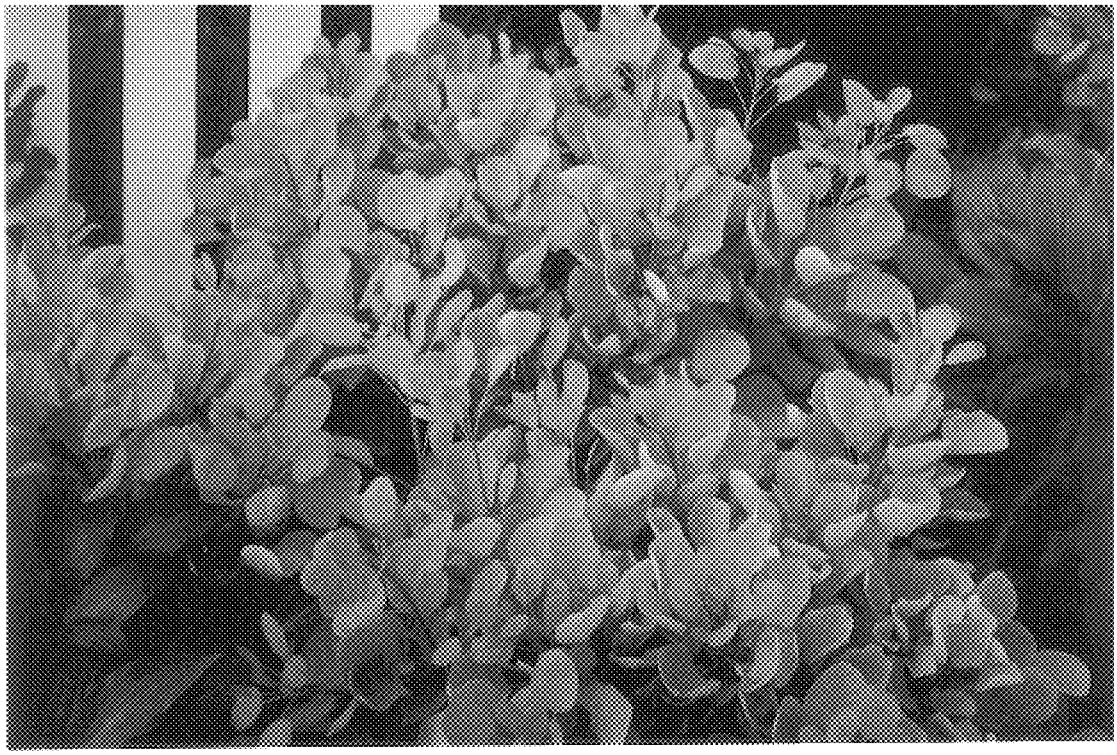

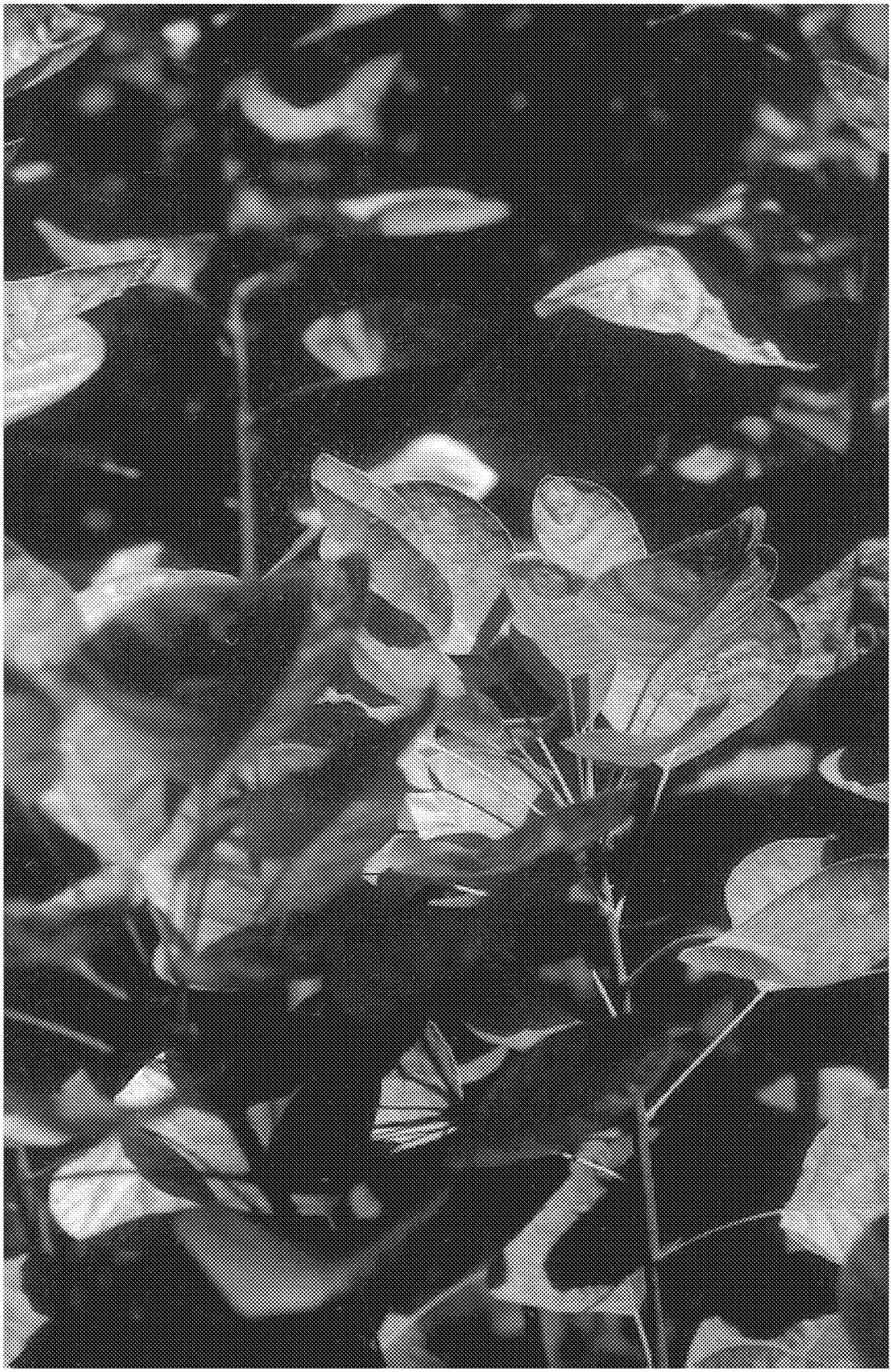

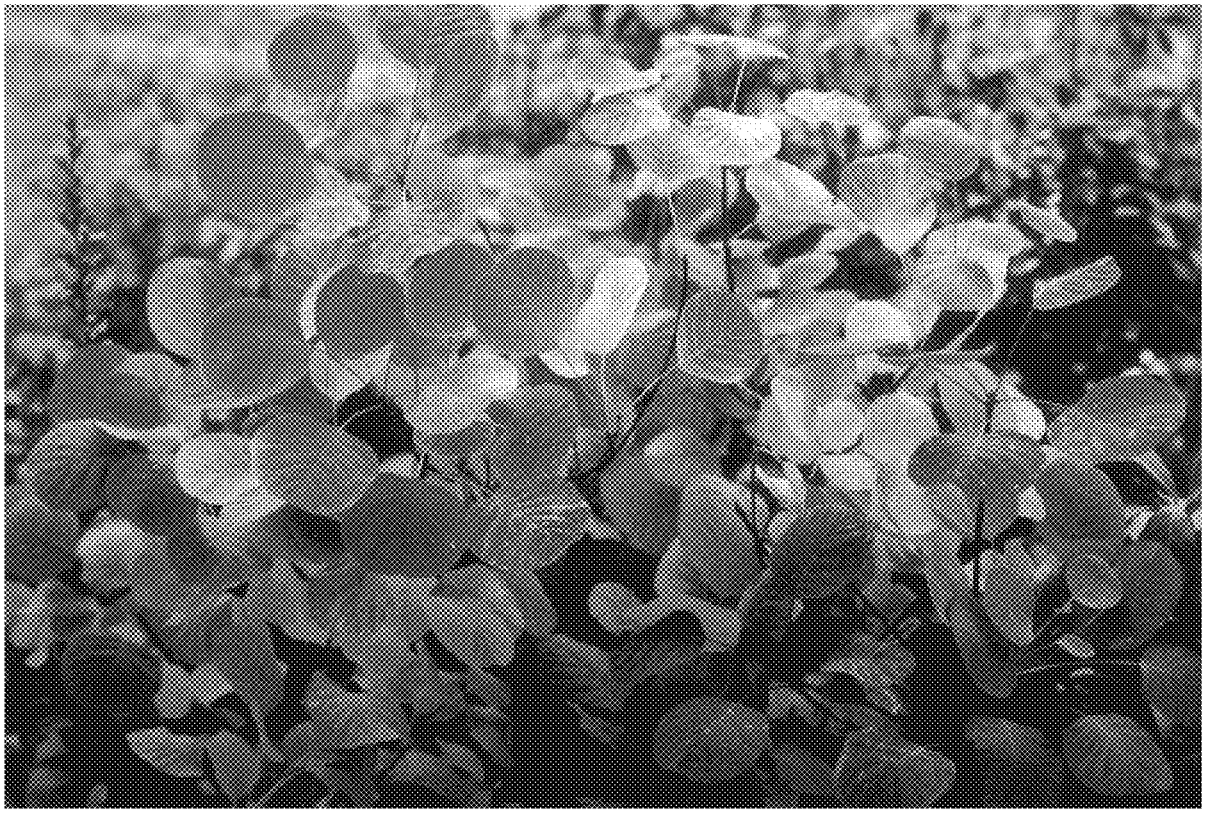

* * * * *